United States Patent

Romano et al.

[11] Patent Number: 5,159,099
[45] Date of Patent: Oct. 27, 1992

[54] CONTINUOUS PROCESS FOR PREPARING DI-ALKYL CARBONATES

[75] Inventors: Ugo Romano, Vimercate; Franco Rivetti, Schio, both of Italy

[73] Assignee: Enichem Synthesis S.P.A., Palermo, Italy

[21] Appl. No.: 742,061

[22] Filed: Aug. 6, 1991

Related U.S. Application Data

[63] Continuation of Ser. No. 420,060, Oct. 11, 1989, abandoned.

[30] Foreign Application Priority Data

Oct. 19, 1988 [IT] Italy .................. 22355 A/88

[51] Int. Cl.$^5$ ............... C07C 68/00; C07C 69/96
[52] U.S. Cl. ................................... 558/277
[58] Field of Search .......................... 558/277

[56] References Cited

U.S. PATENT DOCUMENTS

| 4,360,477 | 11/1982 | Hallgren et al. | 558/277 |
| 4,761,467 | 8/1988 | Bhattacharya | 558/277 |
| 4,785,130 | 11/1988 | Bhattacharya | 558/277 |

Primary Examiner—Vivian Garner
Attorney, Agent, or Firm—Hedman, Gibson & Costigan

[57] ABSTRACT

A continuous process is described for preparing a di-alkyl carbonate, e.g. dimethylcarbonate, via oxidative carbonylation of the corresponding alkanol, e.g. methanol, in the presence of a catalyst system containing a copper alkoxy-halide and water with a mole ratio of the water to the copper salt of between 0.25 and 2.0 and preferably between 0.5 and 1. In this manner extremely high di-alkyl carbonate formation rates are obtained.

9 Claims, 2 Drawing Sheets

CONTINUOUS PROCESS FOR PREPARING DI-ALKYL CARBONATES

This application is a continuation of Ser. No. 07/420,060, filed Oct. 11, 1989, now abandoned.

This invention relates to a continuous process for preparing di-alkyl carbonates. More particularly, the invention relates to a continuous process for preparing dimethylcarbonate (DMC). DMC is an extremely versatile product which is used instead of phosgene in the synthesis of other alkyl and aryl carbonates, which are themselves used as synthetic lubricants, solvents, plasticisers, monomers for organic glasses etc., in methylation and carbonylation reactions, in the preparation of isocyanates, urethanes and polycarbonates, as a fuel additive, as an organic solvent etc.

The classical method of preparing DMC consists of reacting methyl alcohol with phosgene (see for example Kirk-Othmer, Encyclopedia of Chemical Technology, 3rd Ed., Vol. 4, p. 758). This method suffers from numerous technical problems due to the use of phosgene and to the co-production of hydrochloric acid (safety, corrosion, product specifications, need for a hydrochloric acid acceptor with consequent stoichiometric production of NaCl). To obviate these problems various alternative synthesis methods have been studied.

Among these, the oxidative carbonylation of methanol in the presence of suitable catalysts has aroused particular interest in recent years. In particular, it is known to use palladium compounds as catalysts (U.S. Pat. No. 4,361,519, DE-A-3,212,535 and GB-B-2,148,881), the use of which however has two serious drawbacks, namely the co-production of oxalic acid esters [see Fenson, J. Org. Chem., 39, 701 (1974)] and the negative effect of the water co-produced in the reaction, which makes the catalyst system ineffective even at very low concentration levels.

It is also known to use copper compounds (U.S. Pat. No. 3,846,468, U.S. Pat. No. 4,218,391, U.S. Pat. No. 4,318,862, U.S. Pat. No. 4,360,477, U.S. Pat. No. 4,625,044, EP-A-71,286, EP-A-134,668, EP-A-217,651, DE-A-3,212,535 and DE-A-3,016,187) and in particular the use of copper alkoxy-halides of formula Cu(OR)X where R is an alkyl group and X is a halogen atom.

Such catalysts can in fact be conveniently prepared by oxidising the cuprous halide CuX in the initial alkanol with oxygen or air, this forming the basis for the creation of a catalytic cycle in that the subsequent di-alkyl carbonate formation reaction involves the reduction of Cu(II) to Cu(I) in accordance with the following overall reaction scheme:

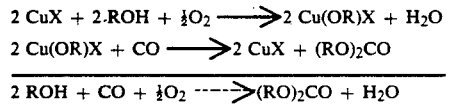

$$2\,CuX + 2\,ROH + \tfrac{1}{2}O_2 \longrightarrow 2\,Cu(OR)X + H_2O$$
$$2\,Cu(OR)X + CO \longrightarrow 2\,CuX + (RO)_2CO$$
$$\overline{2\,ROH + CO + \tfrac{1}{2}O_2 \longrightarrow (RO)_2CO + H_2O}$$

These catalysts can also be used in dispersion, in the absence of organic ligands and/or co-solvents, with many process advantages such as increased simplicity, easier reaction product and catalyst separation, suppression of carbonate hydrolysis by the action of the water co-produced as the result of basic catalysis induced by ligands (such as pyridine), and lower sensitivity of the catalyst system to the co-products $H_2O$ and $CO_2$.

According to previous knowledge in this field, even with these catalyst systems the reaction should preferably be conducted in the presence of a water concentration of less than 1% by weight (see for example EP-A-134,668, page 2, lines 29–30 and EP-A-217,651, page 11, lines 54–55).

Contrary to that suggested by the known art, it has now been observed that if the oxidative carbonylation of a lower alkanol ROH is effected using a catalyst system containing a copper alkoxy-halide under rigorously anhydride conditions, the reaction does not take place in practice.

It has on the other hand been found that if this oxidative carbonylation reaction is effected with a copper alkoxy-halide in the presence of a suitable quantity of water such that the mole ratio of the water to the copper salt is between 0.25 and 2.0 and preferably between 0.5 and 1.0, very high di-alkyl carbonate formation rates are obtained without any negative effect on the selectivity of the reaction. More specifically, it has been found that on subjecting a lower alkanol ROH, where R is a lower alkyl such as methyl, ethyl, propyl or isopropyl and preferably methyl, to oxidative carbonylation in the presence of a catalyst system consisting of a copper alkoxy-halide of formula Cu(OR)X where R has the aforesaid meaning and X is a halogen atom, preferably a chlorine or bromine atom, and more preferably a chlorine atom, the presence of a water quantity having a mole ratio to the copper salt of between 0.25 and 2.0 and preferably between 0.5 and 1.0 enables extremely high di-alkyl carbonate formation rates to be obtained.

This result is surprising considering that the known sensitivity of such catalysts to water would suggest that for best results they should be used under completely anhydrous conditions. When operating according to the invention in the presence of water, the cupric alkoxy-halide undergoes partial hydrolysis, the catalyst system then consisting in practice of a mixture of copper salts of various degrees of halogenation containing halide and hydroxide anions, and characterised by an overall molar halogen/copper ratio of about 1. Such a mixtures can also be formed synthetically starting from cupric halides and oxides, hydroxides or carbonates, the mixture obtained in this manner having the same catalytic behaviour as the cupric alkoxy-halide in the same reaction system.

Figure 1:
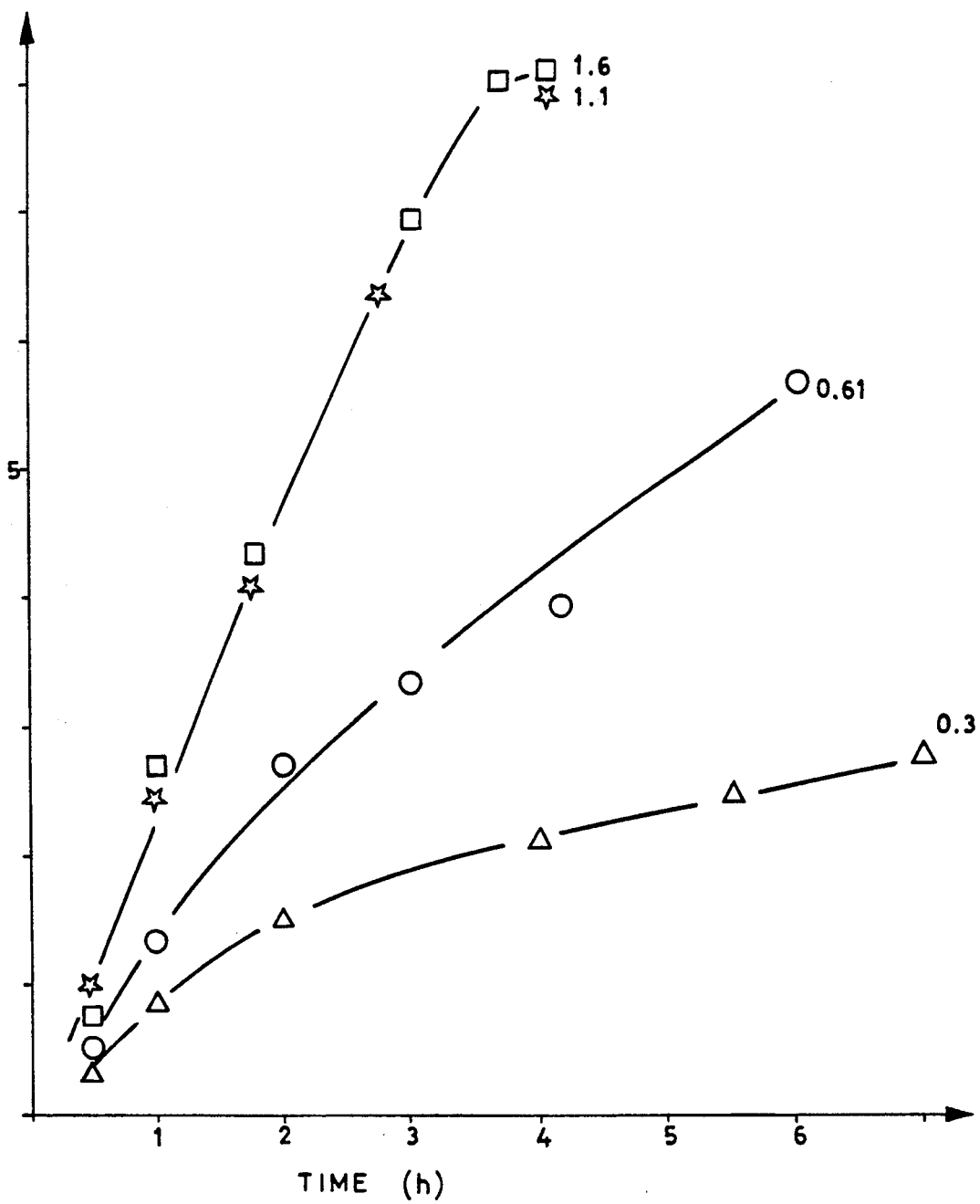
FIGS. 1 and 2 show the formation of DMC being monitored with time.

For the purposes of the present invention, the term "cupric alkoxy-halide" therefore means not only the compound itself but also such a copper salt mixture obtainable by hydrolysing the compound in an aqueous alkanol environment, by oxidising the cuprous halide in an aqueous alkanol environment, or by synthetic formation starting from copper halides and oxides, hydroxides or carbonates.

The present invention therefore provides a continuous process for preparing a di-alkyl carbonate via oxidative carbonylation in the presence of a copper alkoxy-halide, characterised in that the reaction is conducted in the presence of a quantity of water such that the mole ratio of the water to the copper salt is between 0.25 and 2.0, and preferably between 0.5 and 1.0.

The continuous oxidative carbonylation process according to the present invention is conducted in accordance with a general scheme comprising the following steps:

a) feeding the ROH alkanol and the catalyst system containing the copper alkoxy-halide into a reactor into which the carbon monoxide and oxygen flow, adjusting the operating conditions (temperature, pressure, residence time) so that the quantity of water which forms in the reaction is such that the mole ratio of water to copper salt is between 0.25 and 2.0 and preferably between 0.5 and 1.0; and b) separating the reaction product from the effluent liquid, consisting of a mixture of the catalyst system, alkanol, di-alkyl carbonate and water, by conventional methods.

The quantity of copper present in the reaction mixture is not critical and any quantity able to produce the desired catalytic effect can be used.

However, to keep the alkanol conversion percentage as high as possible, according to a preferred aspect of the invention the copper alkoxy-halide is fed in a quantity of between about 10 and about 50 parts, and preferably between about 20 and about 30 parts, of catalyst per 100 parts of alkanol feed.

As already seen, the process of the invention can be used to prepare di-alkyl carbonates, and in particular di-methyl, di-ethyl, di-propyl or di-isopropyl carbonates, although a preferred aspect of the present invention is its use in the preparation of DMC. The copper alkoxy-halide used in the catalyst system of the invention can therefore be a copper methoxy-, ethoxy-, propoxy-or isopropoxy-halide, and preferably a copper methoxy-halide. More preferably, said methoxy-halide is a copper methoxy-bromide or, even more preferably, a copper methoxy-chloride.

The reaction is implemented in practice by dissolving or dispersing the catalyst system in the reaction medium, consisting essentially of the alkanol possibly mixed with an inert solvent such as a hydrocarbon, a halogenated hydrocarbon, an ester or an ether, and passing through this system a stream of oxygen (which can also be in the form of air) and a stream of CO. These streams can be fed either together or separately, and in this latter case either simultaneously or in alternate cycles. It is also possible to use gaseous mixtures containing other gases, such as $H_2$, $N_2$, $CO_2$ or $CH_4$, which behave as inert gases and do not give rise to secondary reactions in the reaction system. In particular, as described in U.S. Pat. No. 4,318,862, it can be convenient to use the carbon monoxide in mixture with hydrogen, e.g. in the form of synthesis gas.

The reaction is conveniently conducted at a temperature of between 50° and 200° C. and preferably between 70° and 150° C., and at a pressure of between atmospheric and 100 atmospheres and preferably between 10 and 100 atmospheres, in that the reaction rate increases with the partial pressure of the carbon monoxide and thus, other conditions being equal, with pressure.

The reaction products can be separated from the effluent by subjecting this latter to thermal flash evaporation under reduced pressure to remove the gases, the alkanol, the di-alkyl carbonate and the water, or depressurizing this effluent and then distilling off the various fractions containing the alkanol, the di-alkyl carbonate and the water.

Other methods known to any expert can also be used in this case to separate the reaction products from the catalyst system and from each other, e.g. reduction of the catalyst and its separation by filtration, and separation of the alkanol, di-alkyl carbonate and water by distillation, possibly using another solvent able to form a suitable azeotrope, distillation of the alkanol and di-alkyl carbonate and removal of the water from the residue by adsorption on molecular sieves, or other conventional methods. The catalyst system and the alkanol, possibly with varying quantities of di-alkyl carbonate, can then be recycled to the carbonylation reactor.

Small quantities of water can be present in the recycled catalyst system, but in such a case by adjusting the operating conditions, as already indicated, the total water quantity (i.e. the water contained in the recycled catalyst system plus the water formed during the reaction) must be made to fall within the stated molar ratio range.

The invention is further illustrated by the following examples.

EXAMPLES 1-4

A dispersion of $Cu(OCH_3)Cl$ (1.68 moles/l) in methanol (100 ml) containing water (in the concentrations indicated in Table 1) is introduced into a 250 ml pressure vessel lined with Teflon ®. The system is placed under carbon monoxide and reacted at 75° C. and 12 atg. the formation of DMC being monitored with time by gas chromatography. The results are given in Table 1 below.

TABLE 1

| Ex No. | mol/l $H_2O$ | DMC concentration (wt %) at t (min) | | | | | | | |
|---|---|---|---|---|---|---|---|---|---|
| | | 30 | 60 | 105 | 120 | 180 | 240 | 330 | 360 |
| 1 | 0.3 | 0.35 | 0.88 | — | 1.50 | — | 2.10 | 2.47 | — |
| 2 | 0.61 | 0.54 | 1.35 | — | 2.75 | 3.40 | — | — | 5.75 |
| 3 | 1.1 | 1.02 | 2.48 | 4.15 | — | — | 7.94 | — | — |
| 4 | 1.6 | 0.79 | 2.75 | 4.88 | — | 6.95 | 8.20 | — | — |

For easier interpretation, these results are summarised graphically in FIG. 1.

EXAMPLES 5-6

A dispersion of $Cu(OCH_3)Cl$ at a concentration of 0.84 mol/l (Ex. 5) and 1.68 mol/l (Ex. 6) in methanol (100 ml) containing water [in a molar water/copper salt ratio of 0.71 (Ex. 5) and 0.63 (Ex. 6)] is introduced into a 250 ml pressure vessel lined with Teflon ®. The system is placed under carbon monoxide and reacted at 75° C. and 12 atg, the formation of DMC being monitored with time by gas chromatography. The results are given in Table 2 below.

TABLE 2

| Ex No. | DMC concentration (wt %) at t (min) | | | | | | | | |
|---|---|---|---|---|---|---|---|---|---|
| | 30 | 60 | 90 | 105 | 120 | 150 | 165 | 210 | 240 |
| 5 | — | 1.75 | 2.97 | — | 4.20 | 4.72 | — | 4.77 | — |
| 6 | 1.04 | 2.45 | — | 4.10 | — | — | 6.35 | — | 7.70 |

Figure 2:
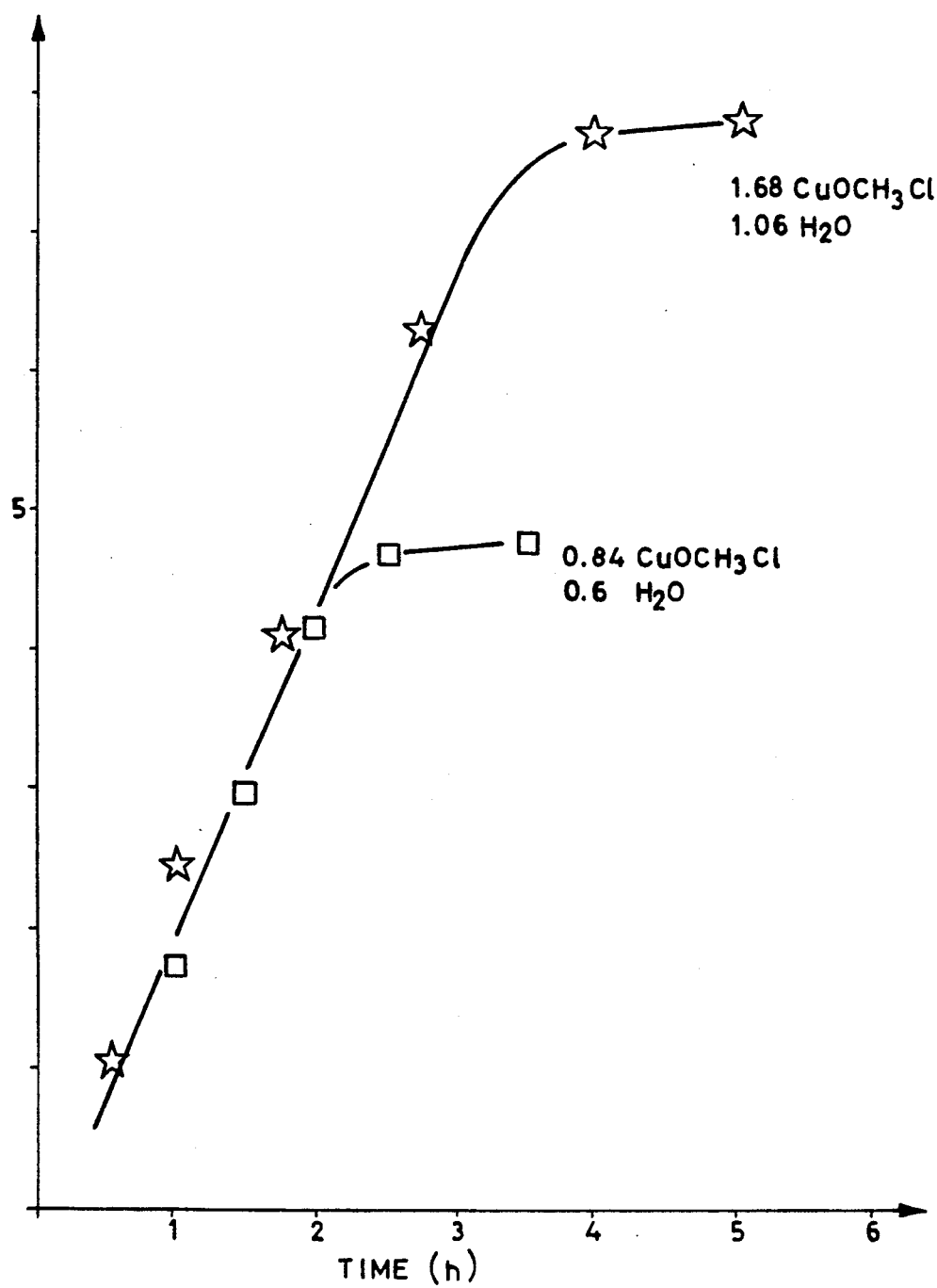

For easier interpretation, these results they are summarised graphically in FIG. 2.

EXAMPLE 7

An internally enamelled continuous stirred reactor having a capacity of 5 liters and fitted with a reflux condenser is fed at 110° C. and 24 atg total pressure with copper methoxy-chloride (2.2 kg/hr) suspended in methanol (8 kg/hr) for a total feed rate of about 10 liters/hr, plus a stream of carbon monoxide (2.6 $Nm^3$/hr) and a stream of oxygen (130 Nl/hr), these latter via distributor dip tubes. The liquid part (8.4 kg/hr) of the reactor effluent (10.6 kg/hr) has the following composition: 10.4 wt % of dimethyl carbonate and 2.1 wt % of water. The gaseous effluent contains CO (98.2%), $CO_2$ (1.6%) and $O_2$ (0.1%).

The productivity is 175 g/l.hr, with a methanol conversion of 8.5%, a selectivity with respect to the methanol of greater than 99%, and a selectivity with respect to the carbon monoxide and oxygen of 85%, the by-product being $CO_2$.

EXAMPLES 8-13

The rate of dimethyl carbonate formation is measured during the reduction of copper methoxychloride (1.68 moles/l) in methanol with carbon monoxide in the presence of different water concentrations is measured at 95° C. and 15 atg total pressure. The observed reaction kinetics show that the reaction is of zero order with respect to the copper methoxy-chloride, thus the dimethyl carbonate formation rate is constant (moles/l.hr). The results are shown in Table 3 below.

TABLE 3

| Ex No. | /$H_2O$///Cu/ moles/l | $R_{DMC}$ (moles/l.hr) |
| --- | --- | --- |
| 8 | 0.20 | 0.20 |
| 9 | 0.31 | 0.33 |
| 10 | 0.43 | 0.57 |
| 11 | 0.56 | 0.74 |
| 12 | 0.68 | 0.76 |
| 13 | 0.95 | 0.75 |

We claim:

1. A continuous process for preparing a di-alkyl carbonate via oxidative carbonylation by reacting the corresponding lower alkanol with carbon monoxide and oxygen in the presence of a catalyst system consisting essentially of a copper alkoxy-halide and a quantity of water such that the mole ratio of the water to the copper salt is between 0.5 and 1.0.

2. The process of claim 1, wherein the lower alkanol is of formula ROX in which R is methyl, ethyl, propyl or isopropyl, and the copper alkoxy-halide is of formula Cu(OR)X in which R is as heretofore defined and X is a halogen atom.

3. The process of claim 2, wherein R is methyl.

4. The process of claim 2 or 3, wherein X is a bromine or chlorine atom.

5. The process of claim 4, wherein X is a chlorine atom.

6. The process of claim 1, wherein the copper alkoxy-halide is used in a weight quantity of between 10 and 50 parts per 100 parts of alkanol.

7. The process of claim 6, wherein the copper alkoxy-halide is used in a weight quantity of between 20 and 30 parts per 100 parts of alkanol.

8. The process of claim 1, wherein the reaction is effected at a temperature of between 50° and 200° C. and a pressure of between 1 and 100 atmospheres.

9. The process of claim 8, wherein the reaction is effected at a temperature of between 70° and 150° C. and a pressure of between 10 and 100 atmospheres.

* * * * *